(12) United States Patent
Voutchkova et al.

(10) Patent No.: US 12,071,386 B2
(45) Date of Patent: Aug. 27, 2024

(54) CONVERSION OF ALCOHOLS AND ALDEHYDES TO ENERGY-DENSE HYDROCARBON FUEL MIXTURES

(71) Applicant: The George Washington University, Washington, DC (US)

(72) Inventors: Adelina M. Voutchkova, Washington, DC (US); Diana Ainembabazi, Washington, DC (US); Darren Dolan, Washington, DC (US); Jonathan Horlyck, Washington, DC (US)

(73) Assignee: THE GEORGE WASHINGTON UNIVERSITY, Washington, DC (US)

( * ) Notice: Subject to any disclaimer, the term of this patent is extended or adjusted under 35 U.S.C. 154(b) by 0 days.

(21) Appl. No.: 18/168,738

(22) Filed: Feb. 14, 2023

(65) Prior Publication Data

US 2023/0257322 A1     Aug. 17, 2023

Related U.S. Application Data

(60) Provisional application No. 63/310,447, filed on Feb. 15, 2022.

(51) Int. Cl.
*C07C 1/24* (2006.01)
*B01J 23/44* (2006.01)
*B01J 35/40* (2024.01)
*C10L 1/04* (2006.01)

(52) U.S. Cl.
CPC ............... *C07C 1/24* (2013.01); *B01J 23/44* (2013.01); *B01J 35/40* (2024.01); *C10L 1/04* (2013.01); *C07C 2523/44* (2013.01); *C10L 2200/0469* (2013.01)

(58) Field of Classification Search
CPC ........ C07C 1/24; C07C 2523/44; B01J 23/44; B01J 35/023; C10L 1/04; C10L 2200/0469
See application file for complete search history.

(56) References Cited

U.S. PATENT DOCUMENTS

2014/0148626 A1* 5/2014 Parimi ................. B01J 35/0013 585/251
2020/0002244 A1* 1/2020 Nesterenko .......... B01J 37/0236

OTHER PUBLICATIONS

Barrett, et al., "A Pinch of Salt Improves n-Butanol Selectivity in the Guerbet Condensation of Ethanol over Cu-Doped Mg/Al Oxides," ACS Sustainable Chem. Eng., Oct. 17, 2018.
Bravo-Suarez, et al., "Vapor-Phase Methanol and Ethanol Coupling Reactions on CuMgAl Mixed Metal Oxides," Applied Catalysis A: General, Jan. 19, 2013.
Cao, et al., "Deoxygenative coupling of 2-aryl-ethanols catalyzed by unsymmetrical pyrazolyl-pyridinyl-triazole ruthenium," Molecular Catalysis 503 (2021).
Larina, et al., "Successive vapour phase Guerbet condensation of ethanol and 1-butanol over Mg-Al oxide catalysts in a flow reactor," Applied Catalysis A: General, Sep. 19, 2019.

(Continued)

*Primary Examiner* — Ali Z Fadhel
(74) *Attorney, Agent, or Firm* — BLANK ROME LLP

(57) ABSTRACT

The present disclosure relates to a process for preparing long-chain alkanes and alkenes from alcohols, aldehydes, or both. The process proceeds via acceptorless dehydrogenation and decarbonylative coupling using a supported catalyst.

19 Claims, 16 Drawing Sheets

(56) References Cited

OTHER PUBLICATIONS

Leon, et al., "Consequences of the iron-aluminum exchange on the performance of hydrotalcite-derived mixed oxides for ethanol condensation," Applied Catalysis B: Environmental 102 (2011).

Leon, et al., "Ethanol catalytic condensation over Mg-Al mixed oxides derived from hydrotalcites," Catalysis Today 164 (2011).

Li, et al., "One-pot synthesis of acidic and basic bifunctional catalysts to promote the conversion of ethanol to 1-butanol," Microporous and Mesoporous Materials 261, Nov. 4, 2017.

Li, et al., "Palladium-Catalyzed Synthesis of N-Cyclohexyl Anilines from Phenols with Hydrazine or Hydroxylamine via N-N/O Cleavage," Adv. Synth. Catal. 10.1002/adsc.201700712, 2017.

Manojveer, et al., "Ru-Catalyzed Completely Deoxygenative Coupling of 2-Arylethanols through Base-Induced Net Decarbonylation," Chem. Eur. J., 2018.

Marcu, et al., "Catalytic valorization of bioethanol over Cu-Mg-Al mixed oxide catalysts," Catalysis Today 147 (2009).

Obora, et al., "Iridium-Catalyzed Reaction of ω-Arylalkanols to α,ω-Diarylalkanes," Angew. Chem. Int. Ed., 2011.

Siqueira, et al., "Highly selective 1-butanol obtained from ethanol catalyzed by mixed metal oxides: Reaction optimization and catalyst structure behavior," Molecular Catalysis 476 (2019).

Wang, et al., "Manganese-Catalyzed Dual-Deoxygenative Coupling of Primary Alcohols with 2-Arylethanols," Angew. Chem. Int. Ed., 2018.

Wang, et al., "Upgrading n-Butanol to Branched Alcohols over Ni/CaxMgyO," ACS Sustainable Chem. Eng., Nov. 3, 2020.

\* cited by examiner

| | | | Atom Economy % | E-factor* |
|---|---|---|---|---|
| 1 |  Obora, 2011 | 1 mol% [Cp*IrPCl₂]₂ / 40 mol% tBuOK, 79% yield | 80.3 | 3.9 |
| 2 |  Liu, 2018 | 1. 0.2 mol% [Mn] / 50 mol% NaOH; [2. Ni@SiO₂-Al₂O₃] H₂, 80% yield e.g. R = H, R₂ = NH₂ | 79.5 / 99.9 | 5.3 / 4.8 |
| 3 |  Johnson, 2018 | 1 mol% [Ru(PPh₃)₃Cl₂]₂ / 1.2 mol% dppp / 60 mol% tBuONa, 86% yield | 79.5 | 38.1 |
| 4 |  Cao, 2021 | 0.1 mol% PPT-Ru / 50 mol% tBuOK, 89% yield | 79.5 | 10.7 |

FIG. 5
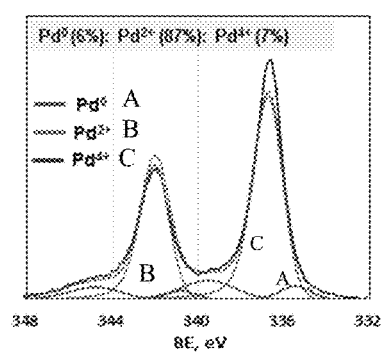
FIG. 5A
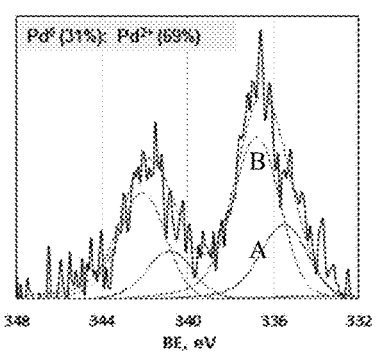
FIG. 5B
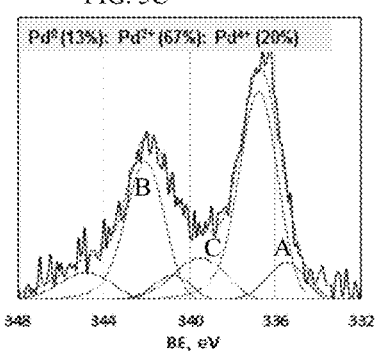
FIG. 5C
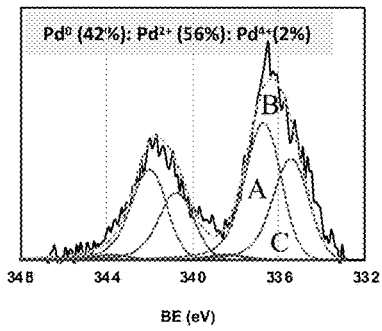
FIG. 5D FIG. 6
FIG. 6A
FIG. 6C
FIG. 6E
FIG. 6G
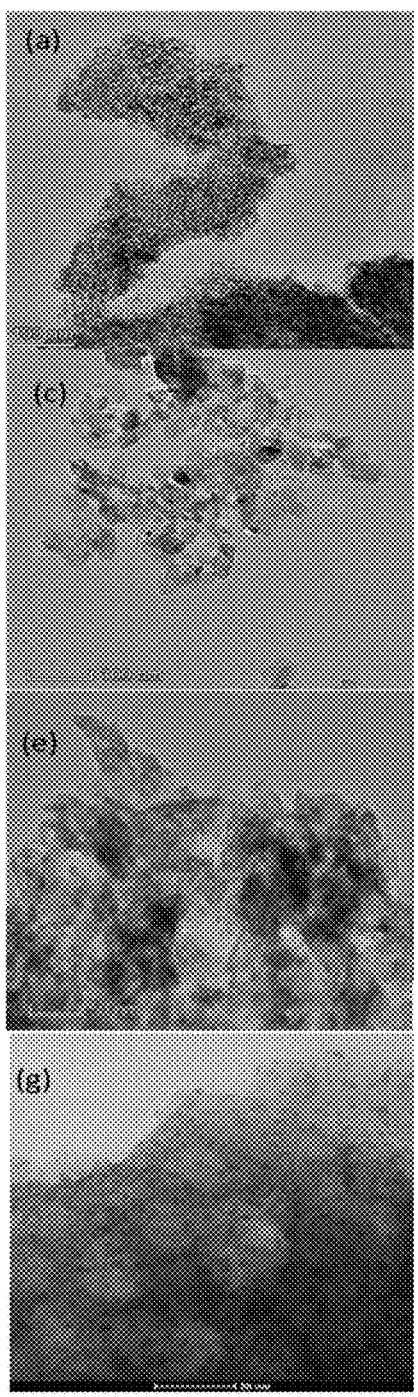
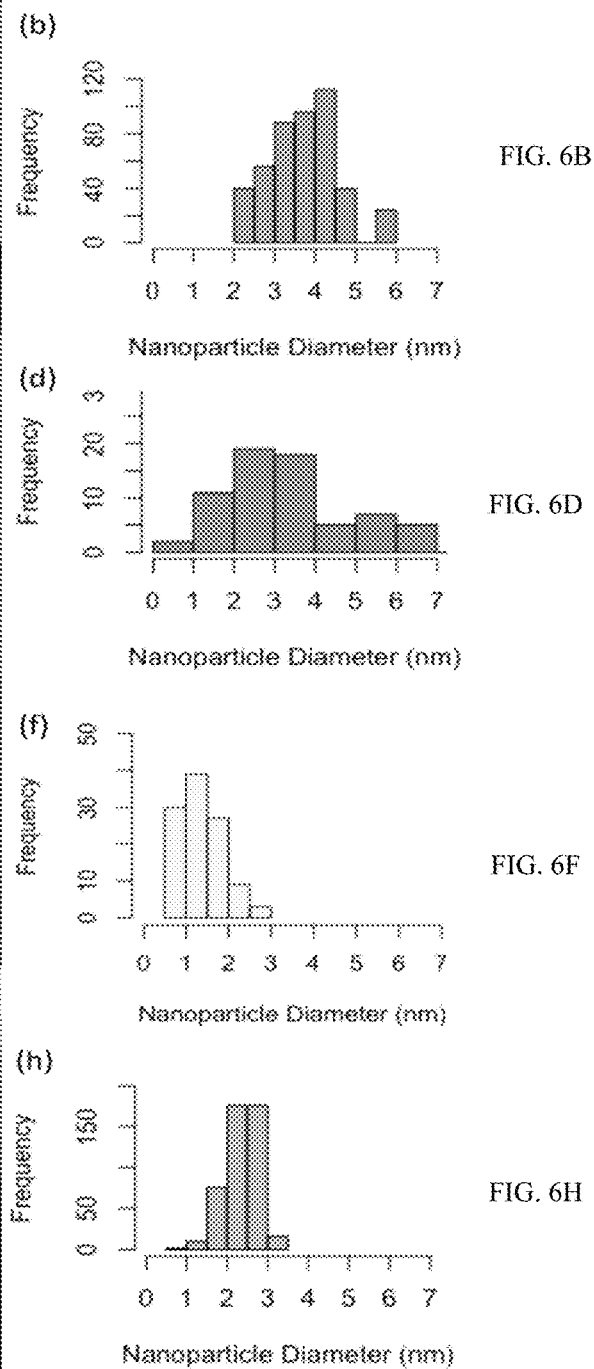
FIG. 6B
FIG. 6D
FIG. 6F
FIG. 6H FIG. 14
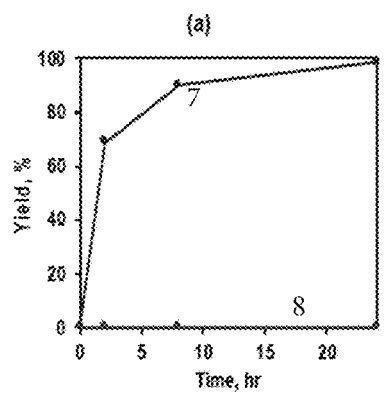 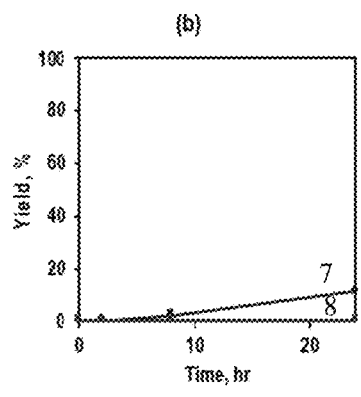 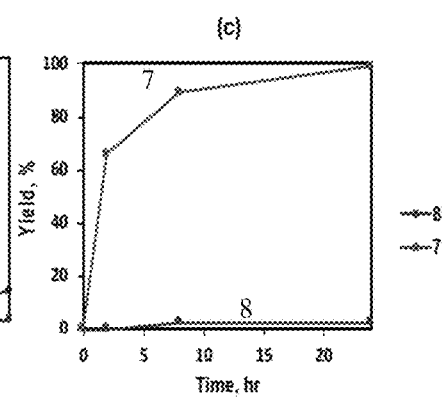
FIG. 14A　　　　　　　FIG. 14B　　　　　　　FIG. 14C FIG. 15
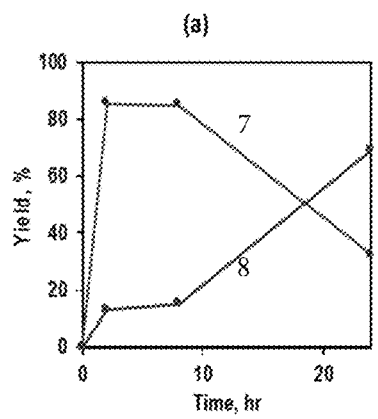
FIG. 15A
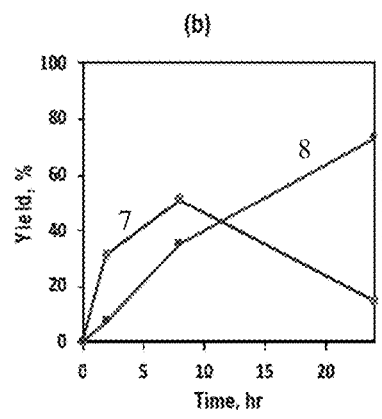
FIG. 15B
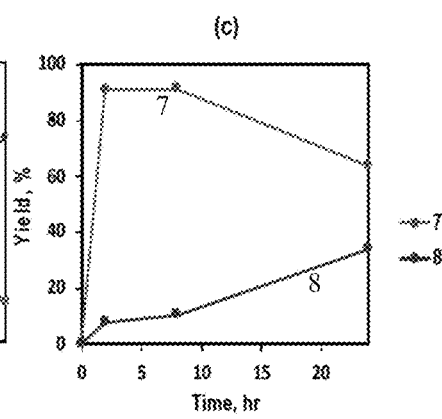
FIG. 15C FIG. 16A
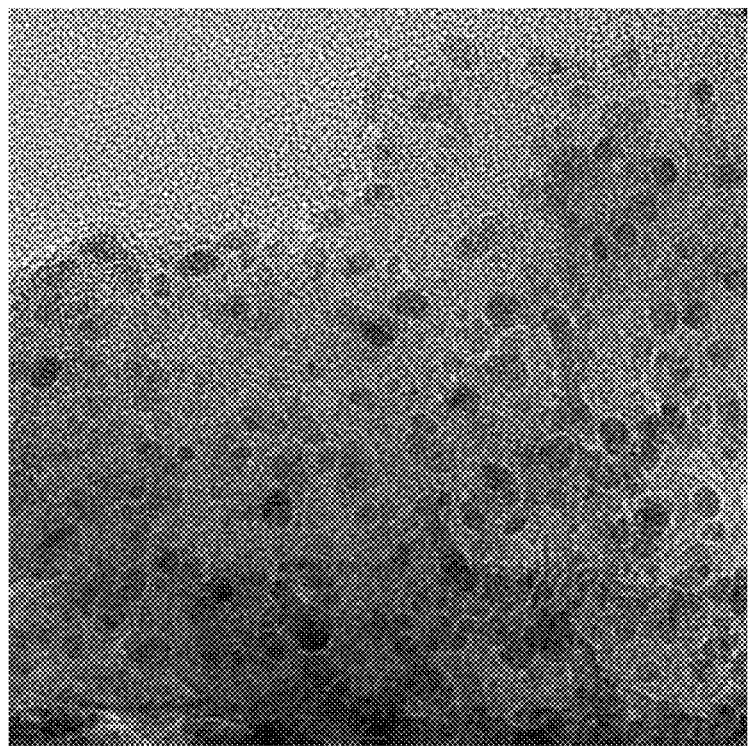
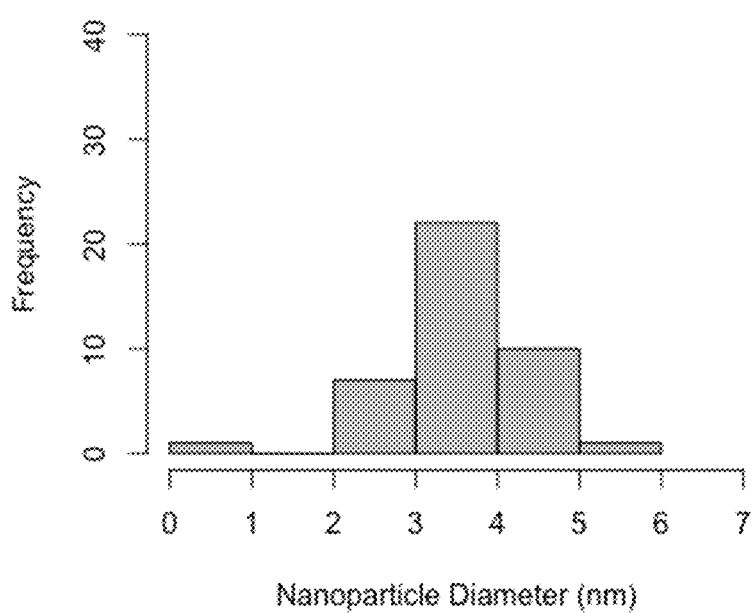
FIG. 16B

CONVERSION OF ALCOHOLS AND ALDEHYDES TO ENERGY-DENSE HYDROCARBON FUEL MIXTURES

CROSS REFERENCE TO RELATED APPLICATIONS

This application claims the benefit of U.S. Provisional Application No. 63/310,447, filed Feb. 15, 2022, the entire contents of which is hereby incorporated by reference.

STATEMENT REGARDING FEDERALLY SPONSORED RESEARCH OR DEVELOPMENT

This invention was made with Government support from the National Science Foundation under Grant/Contract No. 1805080. The Government has certain rights in this invention.

FIELD OF THE INVENTION

The present invention relates to a process for preparing hydrocarbons (such as long-chain alkanes and alkenes) from alcohols, aldehydes, or both. The process proceeds via acceptorless dehydrogenation and decarbonylative coupling using a supported catalyst.

BACKGROUND OF THE INVENTION

The ability to produce liquid hydrocarbon fuels from renewable biomass is an attractive strategy for producing drop-in fuel substitutes with high energy density and platform chemicals for existing petrochemical processes. As renewable sources of alcohols become increasingly abundant, surpassing 100 million metric tons globally for $C_2$-$C_4$ alcohols alone, and increasingly cost-competitive with fossil-fuel alternatives, interest in their catalytic conversion to energy-dense hydrocarbons is also growing, but is yet to be realized in an efficient manner. Practical processes for such transformations should be energy-efficient, use low-cost, robust, heterogeneous catalysts, and be tolerant to aqueous, dilute alcohol feed streams, such as those often derived from fermentation processes. Achieving these objectives requires the design of active and selective supported catalysts tailored for tandem processes for upgrading biomass-derived alcohols. Current approaches to upgrading alcohols primarily rely on the Guerbet condensation, wherein alcohols are coupled to produce longer-chain, branched primary alcohols through a sequence of dehydrogenation, aldol condensation and hydrogenation reactions (see, e.g., Barrett et al., *ACS Sust. Chem. & Eng.*, 6 (11), 15119-15126, 2018). See FIG. 1—Reaction A.

The Guerbet reaction can be catalyzed by supported noble metal catalysts, metal oxides and mixed metal oxides (MMOs). The latter may be derived by calcination of layered double hydroxides (LDHs), and their selectivity tuned through altering the composition and morphology.

While the Guerbet reaction partially deoxygenates alcohols, complete alcohol deoxygenation via deoxygenative olefination (FIG. 1, Reaction B) has only been achieved for 2-aryl ethanol derivatives. Specifically, homogeneous Ir, Ru, and Mn catalysts and a Ru heterogeneous catalyst have been shown to facilitate dehydrogenation of 2-aryl ethanols, followed by base-promoted aldol condensation and decarbonylation. See FIG. 2 and Obora et al. *Angewandte Chemie Int. Ed.*, 50(37), 8618-8622, 2011; Wang et al., *Angewandte Chemie Int. Ed.*, 57(46), 15143-15147, 2018; Manojveer et al., *Chemistry—A European Journal*, 24(4), 803-807, 2018; and Cao et al., *Molecular Catalysis* 503, 111391, 2021. The challenge with these systems, however, is the utility of the base which consequently results in copious amounts of waste that is generated at the end of the reaction.

MgO and γ-$Al_2O_3$ supported metal catalysts present different divergent acid-base properties. Pt-supported MgO displays strong basicity, whereas Pt-$Al_2O_3$ displays strong acidity. Similar observations have been made for Pd analogues. See, e.g., Saad et al., *Appl. Catal.*, A, 544, 1-9, 2017, and Groppo et al., *J. Phys. Chem. C, III* (19), 7021-7028, 2007.

Hydrotalcites (HTs) are a sub-set of LDHs with general formula:

$$[M^{2+}_{1-x}M^{3+}_x(OH)_2]^{x+}(A^{n-})_{x/n} \cdot mH_2O,$$

where $M^{2+}$ and $M^{3+}$ are, e.g., $Mg^{2+}$ and $Al^{3+}$ or compatible alkali earth and transition metal cations, x is, e.g., in the range of about 0.1 to about 0.33, n is the charge of the anion (e.g., −1 or −2) and m is, e.g., a whole number. Although LDH materials similar to the present HT exhibit basic properties approaching those of MgO, the tunable nature of such materials means that both $O^{2-}$ and $Al^{3+}$ respective Lewis base and acid centres are accessible.

There is therefore a need for new efficient atom-economical processes to convert alcohols and aldehydes to long-chain alkanes and alkenes. The present invention addresses such needs in a one-pot, hydrogen free and base free process.

SUMMARY OF THE INVENTION

The present inventors have surprisingly found that alcohols and aldehydes may be converted to long-chain alkanes and alkenes via acceptorless dehydrogenation and decarbonylative coupling using multifunctional Pd catalysts and supports possessing different acid-base properties. The product mixture can be tuned to suit fuel needs, e.g., from petroleum to jet fuel, by changing the starting alcohol and the catalyst used.

Without wishing to be bound by theory, the present inventors theorize that the significantly higher barrier for decarbonylation than aldol condensation controls the reaction sequence such that initial alcohol dehydrogenation affords the aldehyde, which then undergoes stepwise aldol condensation and decarbonylation to the alkene. See FIG. 3.

Effecting the requisite tandem transformations in a one-pot reaction (to minimize reactor complexity and cost) necessitates multifunctional catalysts possessing catalytic sites effective for dehydrogenation, aldol condensation and decarbonylation. Optimizing the formulation and operation of multifunctional catalysts is challenging, since it hinges on controlling the activity and selectivity of several interdependent steps. In turn, this requires control over the size, location and structure of catalytically active species, and mechanistic insight into corresponding structure-activity relationships, including the role of supports.

The unique reactivity of palladium (Pd) doped-LDH (or HT) catalysts includes decarbonylation of aldehydes, aldol condensations and acceptorless alcohol and amine dehydrogenation.

The present inventors have developed an innovative alcohol upgrading and deoxygenation cascade that produces only water, hydrogen and carbon monoxide. This hydrogen-free cascade is catalyzed by multifunctional paladium catalysts, whose supports offer diverse acid-base properties (such as, but not limited to, primarily basic MgO, acidic γ-$Al_2O_3$ and Mg—Al hydrotalcite (HT) with a combination of Lewis acidic and basic sites).

Accordingly, in one aspect, the present invention relates to a process for preparing a hydrocarbon (such as an alkane, an alkene, or a mixture thereof).

In one embodiment, the process comprises
(i) reacting an alcohol, an aldehyde, or both, with a catalyst to form a hydrocarbon; wherein the catalyst comprises palladium (e.g., ions, atoms, particles) and a support.

In one embodiment, the process comprises
(i) reacting an alcohol with catalyst to form a hydrocarbon;
wherein the catalyst comprises palladium (e.g., ions, atoms, particles) and a support.

In one embodiment, the process comprises
(i) reacting an aldehyde with a catalyst to form a hydrocarbon;
wherein the catalyst comprises palladium (e.g., ions, atoms, particles) and a support.

In one embodiment, the process is conducted in the absence of a solvent.

In one embodiment, the process is conducted in the presence of a solvent. Suitable solvent that may be used include, but are not limited to, aromatic hydrocarbons (e.g., toluene), ethers (e.g., tetrahydrofuran), ethanol, and any combination thereof.

In one embodiment, the alcohol is a primary alcohol, a secondary alcohol, a tertiary alcohol, a diol, a polyol, or any combination thereof. The alcohol may be linear or branched. The alcohol may also be a cyclic (monocyclic or polycyclic) alcohol. The alcohol may also be substituted with one or more additional functional groups (in addition to hydroxyl group(s)), such as, for example, ketones, imines, carboxylic acids, thiols, or any combination thereof.

In one embodiment, the alcohol is an aliphatic alcohol, such as an aliphatic alcohol having a methylene (—$CH_2$—) group adjacent to the hydroxyl bearing carbon atom. The aliphatic alcohol my contain one or more additional substituted or unsubstituted aromatic (e.g., substituted or unsubstituted phenyl) groups.

In one embodiment, the alcohol is selected from methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, heneicosanol, docosanol, tricosanol, tetracosanol, pentacosanol, hexacosanol, heptacosanol, octacosanol, nonacosanol, triacontanol, glycerol, hexitol, sorbitol, 1,2-butadiol, 1,4-butadiol, arabinol, xylose, 2-deoxyhexopyranose, 1,4-anhydroxylitol, 1,5-gluconolactone, and any combination of any of the foregoing.

In one embodiment, the particle size of the palladium particles ranges from sub-nano (i.e., cannot be observed by TEM) to about 10 nm, such as between about 1 nm and about 10 nm, or between about 2 nm and about 5 nm.

In one embodiment, the support is a basic support, an acidic support, an amphoteric support, or any combination thereof. In one embodiment, the support is a clay-based support (e.g., a clay-based support having Lewis acidic and Bronsted basic sites). In one embodiment, the support is a hydrotalcite support having varying strength and quantity of acidic and basic sites, with basic sites predominating.

In one embodiment, the particle size of the support ranges between about 10 nm and about 400 nm.

In one embodiment, the support is selected from magnesium oxide, hydrotalcite, montmorillonite, alumina, vermiculite, kaolinite, talc, nontronite, saponite, illite, amosite, chamosite, cookeite, nimite, dickite, nacrite, pyrophyllite, and any combination thereof.

In one embodiment, the support is selected from magnesium oxide, hydrotalcite, montmorillonite, vermiculite, kaolinite, talc, nontronite, saponite, illite, amosite, chamosite, cookeite, nimite, dickite, nacrite, pyrophyllite, and any combination thereof.

In one embodiment, the support is magnesium oxide. In one embodiment, the support is hydrotalcite, e.g., $Mg_6Al_2CO_3(OH)_{16}\cdot 4\ H_2O$.

In one embodiment, the catalyst comprises between about 0.1 mol. % and about 10 mol %, such as between about 1 mol. % and about 5 mol. %, of palladium (e.g., grams of palladium relative to grams of catalyst).

In one embodiment, the support further comprises a dopant, e.g., one or more metals in addition to palladium.

In one embodiment, the dopant is a metal selected from Fe, Cu, Ni, Zn, Co, or any combination of any of the foregoing. In one embodiment, the dopant completely replaces Mg and/or Al.

In one embodiment, the support comprises between about 0 mol. % and about 40 mol. % of a dopant.

In one embodiment, the process is conducted at a temperature of between about 100° C. and about 200° C., such as between about 120° C. and about 150° C., or between about 150° C. and about 180° C. In one embodiment, the process is conducted at a temperature of about 180° C.

In one embodiment, the process proceeds via a deoxygenative coupling reaction.

In one embodiment, the process proceeds via a tandem dehydrogenation, aldol condensation and decarbonylation reaction.

In one embodiment, the yield of the hydrocarbon ranges between about 10% and about 97%.

In one embodiment, the selectivity of the hydrocarbon product formed during the process (e.g., the concentration of alkane/alkene product(s) relative to all products formed during the process) ranges between about 40% and about 98.

In one embodiment, the process proceeds with an atom economy of between about 80% and about 95%. In one embodiment, the waste products formed during the process (i.e., the non-alkane/alkene product(s)) comprises carbon dioxide, water, residual hydrogen gas, and any combination thereof.

In one embodiment, the ratio of waste (e.g., carbon dioxide, water, residual hydrogen gas, and any combination thereof) to alkane/alkene hydrocarbon product formed during the process (E-factor) is between about 0.02 and about 0.1.

In one embodiment, the ratio of waste (e.g., carbon dioxide, water, residual hydrogen gas, and any combination thereof) to alkane/alkene hydrocarbon product formed during the process (E-factor) is less than about 0.02, such as less than about 0.01, or less than about 0.005.

In another aspect, the present invention relates to a hydrocarbon (e.g., an alkane/alkene product) prepared by a process according to any of the embodiments described herein.

In another aspect, the present invention relates to a fuel (e.g., a jet fuel) prepared by a process according to any of the embodiments described herein.

BRIEF DESCRIPTION OF THE DRAWINGS

FIG. 5 shows palladium 3d X-ray photoelectron spectra of (a) Pd—$Al_2O_3$(FIG. 5a), 5% Pd-HT (FIG. 5b), Pd—MgO (FIG. 5c), and 1% Pd-HT (FIG. 5d).

FIG. 6 shows bright field TEM images and corresponding palladium particle size distributions for Pd—$Al_2O_3$(FIGS. 6a and 6b), Pd—MgO (FIGS. 6c and 6d), 1% Pd-HT (FIGS. 6e and 6f), and 5% Pd-HT (FIGS. 6g and 6h).

FIG. 14 shows the time course of decarbonylative olefination of heptanal (see Scheme 1) using 5% Pd-HT (FIG. 14a), Pd—$Al_2O_3$(FIG. 14b) and Pd—MgO (FIG. 14c) at 100° C.

FIG. 15 shows the time course of decarbonylative olefination of heptanal using Pd-HT (5%) (FIG. 15a), Pd—$Al_2O_3$(FIG. 15b), and Pd—MgO (FIG. 15c) at 150° C., under air.

FIG. 16 shows the TEM image (FIG. 16a) of used Pd-HT (5%) and the corresponding particle size distribution (FIG. 16b). The mean particle size is 3.3±0.5 nm.

DETAILED DESCRIPTION OF THE INVENTION

Figure 1:
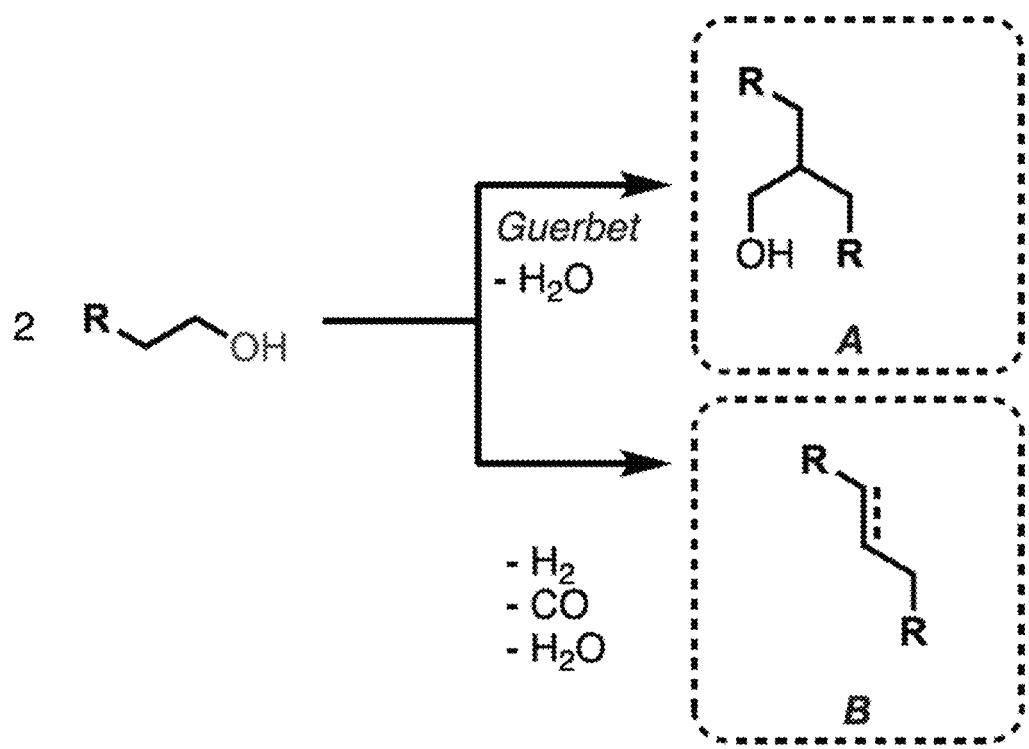
FIG. 1 shows a process for upgrading primary alcohols to longer chain alcohols (FIG. 1(a)) and hydrocarbons (FIG. 1(b)).
Figure 2:
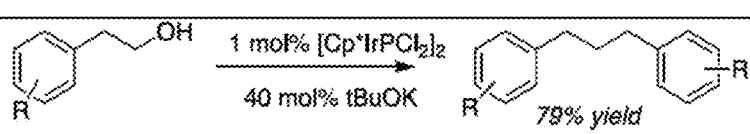
FIG. 2 shows alcohol coupling processes for 2-aryl ethanol derivatives facilitated by homogeneous Ir, Ru and Mn catalysts.
Figure 2:
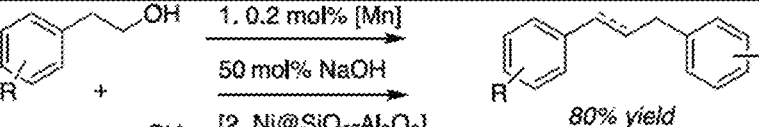
Figure 2:
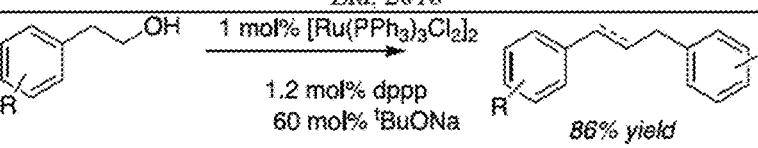
Figure 2:
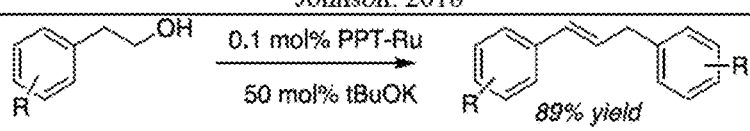

As used herein, the term "acceptorless dehydrogenation" may refer to the oxidation of an alcohol to an aldehyde or ketone without use of any external oxidant and with extrusion of hydrogen.

As used herein, the terms "atom-economical" and "atom economy" may refer to the conversion efficiency of a chemical process in terms of all atoms involved and the desired products produced (e.g., equal to the ratio between the mass of desired product to the total mass of products, expressed as a percentage).

As used herein, the term "deoxygenative coupling" may refer to a reaction in which a carbon-carbon bond is formed between two components and the total oxygen content of the final product is lower than the sum of its parts.

As used herein, the term "tandem dehydrogenation" may refer to a reaction in which an alcohol undergoes oxidation to an aldehyde, which then undergoes a subsequent reaction to form another product.

As used herein, the term "aldol condensation" may refer to a reaction in which an enol or an enolate ion reacts with a carbonyl compound to form a β-hydroxyaldehyde or β-hydroxyketone, followed by dehydration to give a conjugated enone.

As used herein, the term "decarbonylation" may refer to a reaction that involves the loss of carbon monoxide (CO) from an organic substrate to form a new product, such as an aldehyde forming an alkane and CO.

Catalyst Characterization

Physicochemical properties and palladium composition of Pd—$Al_2O_3$, Pd—MgO and Pd-HT (1% and 5%) catalysts were investigated by inductively coupled plasma atomic emission spectroscopy (ICP-AES), Brunauer-Emmett-Teller analysis (BET) Barrett-Joyner-Halenda analysis (BJH), transmission electron microscopy (TEM), X-ray photoelectron spectroscopy (XPS) and powder X-ray diffraction (PXRD). The palladium content, surface area, pore volume and size of the catalysts are shown in Table 1. PXRD patterns of (a) Pd—$Al_2O_3$ and $Al_2O_3$; (b) 5% Pd-HT and HT; (c) Pd—MgO and MgO, and (d) Cu, Co, Ni and Fe doped Pd-x-HTs are shown in FIG. 4.

TABLE 1

| Catalyst | Palladium loading[a] (wt. %) | Surface area[b] ($m^2$/g) | Pore volume[b] ($cm^3$/g) | Pore size[c] (nm) | Pd/PdO particle size (nm) TEM | Pd/PdO particle size (nm) PXRD | Pd phases identified by High Resolution TEM (HRTEM) |
|---|---|---|---|---|---|---|---|
| Pd—$Al_2O_3$ | 1.95 | 83 | 0.116 | 8.8 | 3.7 ± 0.9 | — | Pd (111) |
| Pd—MgO | 2.30 | 45 | 0.588 | 46.5 | 3.5 ± 1.0 | 4.7 ± 0.8 | could not be identified |
| 5% Pd-HT | 5.15 | 53 | 0.132 | 6.6 | 2.4 ± 0.4 | — | Pd (111) |
| 1% Pd-HT | 0.99 | | | | 1.5 ± 0.5 | | Pd (111) PdO (110) |

[a]Data from ICP-AES; [b]Data from BET analysis; [c]Data from BJH analysis.

Powder XRD of Pd—$Al_2O_3$ and Pd-HT (1% and 5%) only show reflections for the respective supports, indicating that the palladium is highly dispersed. The diffractogram of Pd—MgO, however, shows reflections associated with crystalline PdO phases, in addition to reflections characteristic of brucite nanocrystals. See FIG. 4.

XPS revealed significant differences in palladium surface speciation for the three catalysts. See FIG. 5. All catalysts comprise $Pd^{2+}$ as the major species in addition to $Pd^0$, with Pd—MgO and Pd—$Al_2O_3$ also exhibiting a low level of $Pd^{4+}$. The $Pd^{2+}$ surface concentration was highest for Pd—$Al_2O_3$, whereas Pd-HT shows the greatest $Pd^0$ concentration, suggesting that the support acid-base properties impact Pd speciation.

Corresponding TEM images (see FIG. 6) reveal oxide agglomerates decorated with palladium nanoparticles typical of wet impregnation syntheses. Nanoparticles (NPs) dispersed over $Al_2O_3$ 5% HT and 1% HT supports exhibited size and shape uniformity, with mean diameters of 3.7 nm, 2.4 nm and 1.5 nm, respectively. HRTEM of 1% Pd-HT show Pd(111) and PdO(110) phases, while Pd—$Al_2O_3$ shows only Pd(111). No lattice fringes were observable by TEM for Pd—MgO, and hence the nature of the corresponding Pd phase could not be directly assigned. However, XRD identified reflections consistent with PdO (101), (112) and (220) planes. TEM images and corresponding particle size distributions for the Fe, Co, Ni, Cu and Zn doped Pd-HTs are shown in FIG. 7.

Figure 3:
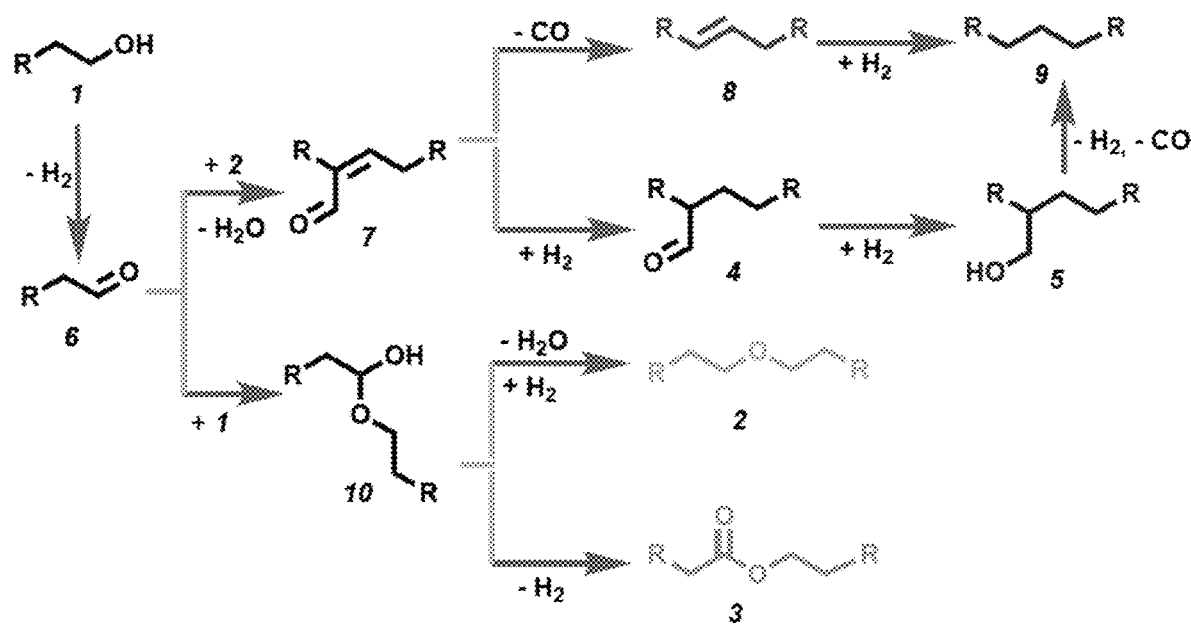
FIG. 3 shows an exemplary proposed mechanism for the conversion of alcohols to alkenes, alkanes and additional by-products.
Figure 4A:
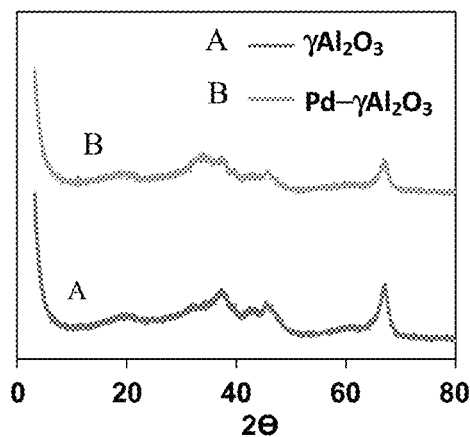
FIG. 4 shows powder XRD patterns of Pd—$Al_2O_3$ and $Al_2O_3$(FIG. 4a), 5% Pd-HT and HT (FIG. 4b), Pd—MgO and MgO (FIG. 4c), and doped Pd-x-HTs (5%) (x=Zn, Cu, Ni, Co, Fe) (FIG. 4(d)).
Figure 4B:
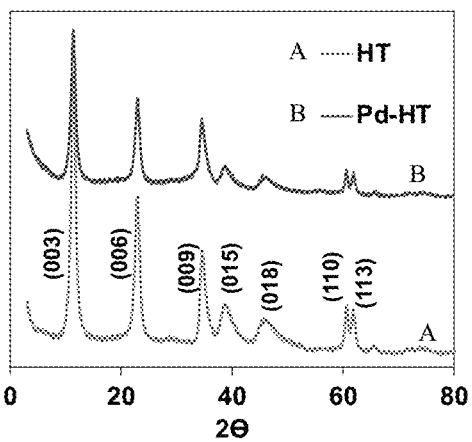
Figure 4C:
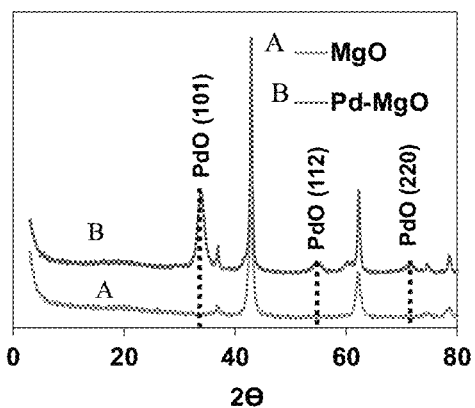
Figure 4D:
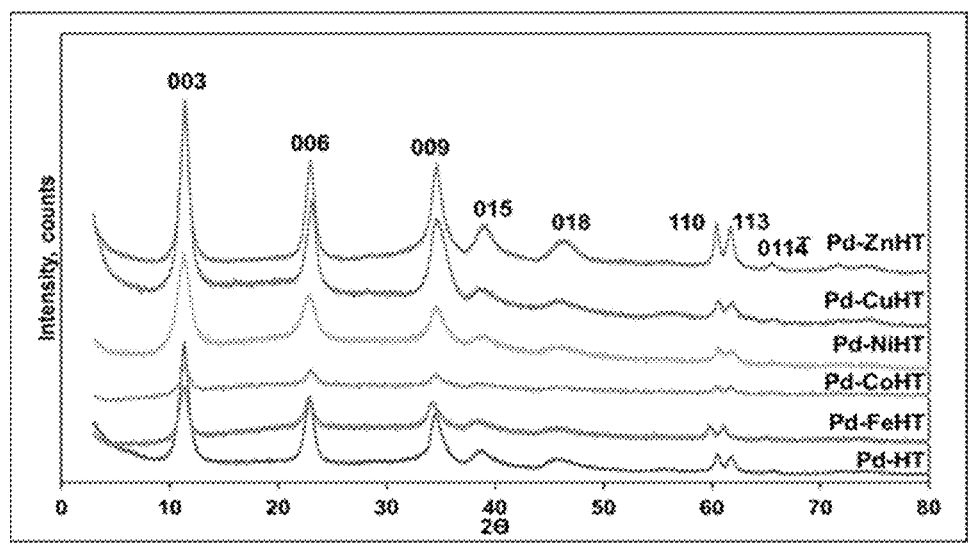
Figure 7A:
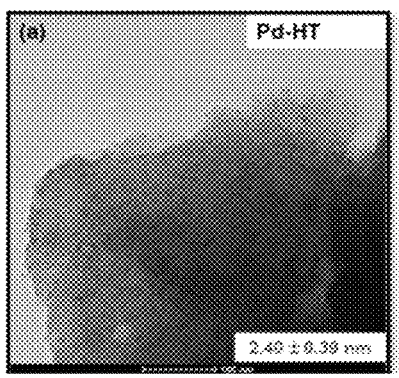
FIG. 7 shows TEM images and corresponding palladium particle size distributions for Pd-HT (5%) (FIG. 7a) and doped Pd-HTs (5%) (Fe.
FIG. 7b, Co.
FIG. 7c, Ni.
FIG. 7d, Cu.
FIG. 7e, and Zn.
FIG. 7f).
Figure 7B:
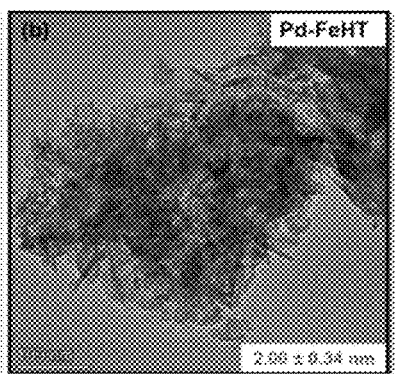
Figure 7C:
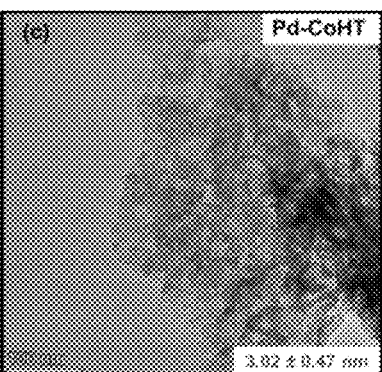
Figure 7D:
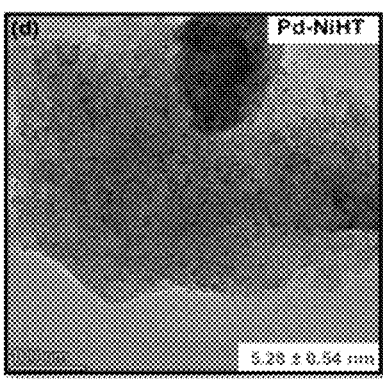
Figure 7E:
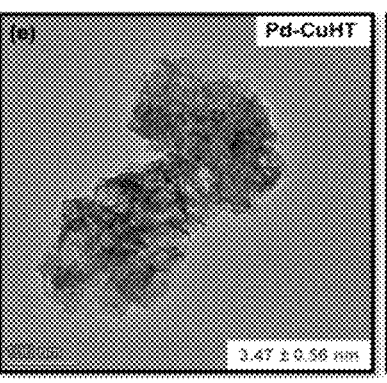
Figure 7F:
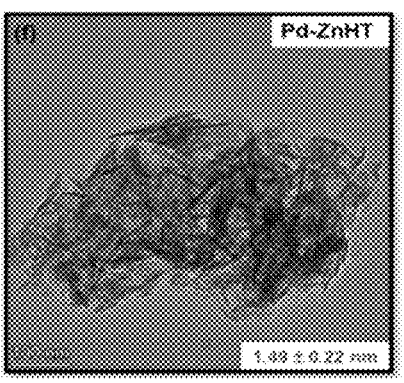

The palladium catalysts were subsequently tested for alcohol coupling using heptanol 1 as the substrate at 180° C. The proposed mechanism for the process is shown in FIG. 3. Initial dehydrogenation produces aldehyde 6, which can either undergo ketal hydrogenolysis to form ether 2, alcohol coupling and dehydrogenation to form ester 3, or aldol condensation to form 7. Double transfer hydrogenation (TH) of 7 (with hydrogen atoms from alcohol dehydrogenation) forms the Guerbet alcohol 5. Alternatively, decarbonylation of 7 forms alkene 8, which can be hydrogenated to alkane 9 over palladium metal. The selectivity for Guerbet alcohol 5 is promoted by co-operative acid and base catalysis, as possible for Pd-HT.

Control reactions with Pd-free MgO, HT and γ-$Al_2O_3$ supports showed no heptanol conversion. Pd—$Al_2O_3$ afforded >90% alcohol conversion in 48 hours, with diheptyl ether as the major product (2, 97% selectivity). Only trace heptyl heptanoate 3 was observed and no alkene products were observed. See FIG. 8 and Table 2 below. This high ether selectivity may be attributed to Pd-catalyzed ketal hydrogenolysis, proceeding via heptanal, or acid-catalyzed alcohol dehydration over strong Lewis acidic $Pd^{\delta+}$ sites. Palladium participation may be inferred from the fact that γ-$Al_2O_3$ affords no conversion with either heptanol, nor heptanal and heptanol.

TABLE 2

| Catalyst | 2 | 3 | 5 | 8 | 9 | 6 | Conversion (%) |
|---|---|---|---|---|---|---|---|
| 5% Pd—HT | 2 | 11 | 23 | 3 | 12 | 0 | 51 |
| 1% Pd—HT | 3 | 21 | 5 | 14 | 15 | 0 | 58 |
| Pd/MgO | 0 | 4 | 0 | 5 | 8 | 0 | 17 |
| Pd/$Al_2O_3$ | 88 | 3 | 0 | 0 | 0 | 0 | 91 |
| 2% Ag—CuHT | 0 | 24 | 25 | 0 | 0 | | 50 |
| Pd/C | 0 | 78 | 4 | | | | 83 |
| Ru/HT | 0 | 17 | 25 | 5 | | | 60 |
| 5% Pd—FeHT | 0 | 9 | 60 | 1 | 6 | 1 | 99 |
| 5% Pd—CoHT | 0 | 12 | 11 | 1 | 4 | 1 | 32 |
| 5% Pd—NiHT | 0 | 2 | 2 | 1 | 1 | 0 | 5 |
| 5% Pd—CuHT (<5% Cu) | 0 | 31 | 0 | 1 | 8 | 1 | 84 |
| 5% Pd-CuHT | 0 | 48 | 14 | 0 | 0 | 1 | 95 |

A comparable reaction with Pd-HT (1% and 5%) affords negligible quantity of the ether 2. Instead, near complete selectivity for products arising from initial alcohol dehydrogenation is observed (FIG. 3): 46% selectivity for Guerbet alcohol 5, 7% for 6-E-tridecene 8, 22% for tridecane 9 and 22% for ester 3 (with 50% alcohol conversion). Pd-HT is therefore significantly more efficient at facilitating the initial alcohol dehydrogenation than Pd—$Al_2O_3$, likely due to the higher concentration of palladium metal sites.[12] Product selectivity is dictated by the subsequent fate of heptanal: reaction with the parent alcohol and dehydrogenation forms the ester 3, whereas aldol condensation affords 7, which in turn unlocks access to saturated oxygenates 4 and 5, or alkenes/alkanes 8/9. The molar ratio of ester 3 to the observed aldol reaction products (5, 8 and 9) of 1:3.6 evidences that the strong basic sites in the HT support promote aldol condensation.[14] In contrast, the lack of basic sites and weak acidic sites on γ-$Al_2O_3$ promote ether 3 formation by either dehydration or ketal hydrogenolysis.

Since downstream hydrogenation is dependent on the rate of the upstream dehydrogenation, the selectivity for 5 versus hydrocarbons 8 and 9, (~2:1 for Pd-HT) reflects the relative rates of re-hydrogenation versus decarbonylation of the reactively-formed aldol product 7. High selectivity to hydrocarbons requires faster decarbonylation, which is dependent on the Pd speciation.

Pd-HTs with Fe, Cu, Zn and Co dopants were also examined. Compared to the Pd-HT, Pd-ZnHT and Pd-FeHT afforded significantly more Guerbet alcohol 5, suggesting they are more efficient at transfer hydrogenation vs. decarbonylation. Pd-CuHT afforded primarily the ester 3, consistent with the expected lower basicity of the CuHT which disfavors aldol at the expense of dehydrogenation. Varying the amount of Cu in the Pd-CuHTs affected the selectivity significantly, showing that the dopant quantity can be used to further optimize selectivity.

Compared to the other catalysts, Pd—MgO was significantly less active for heptanol conversion (16%) but exhibited the highest selectivity for hydrocarbons 8 (29%) and 9 (50%), alongside ester 3. These observations suggest that Pd—MgO possesses few or weak Lewis acidic sites and limited palladium metal sites, accounting for slow dehydrogenation and no dehydration. These features also favor decarbonylation over re-hydrogenation of the aldol condensate 7.

Figure 9:
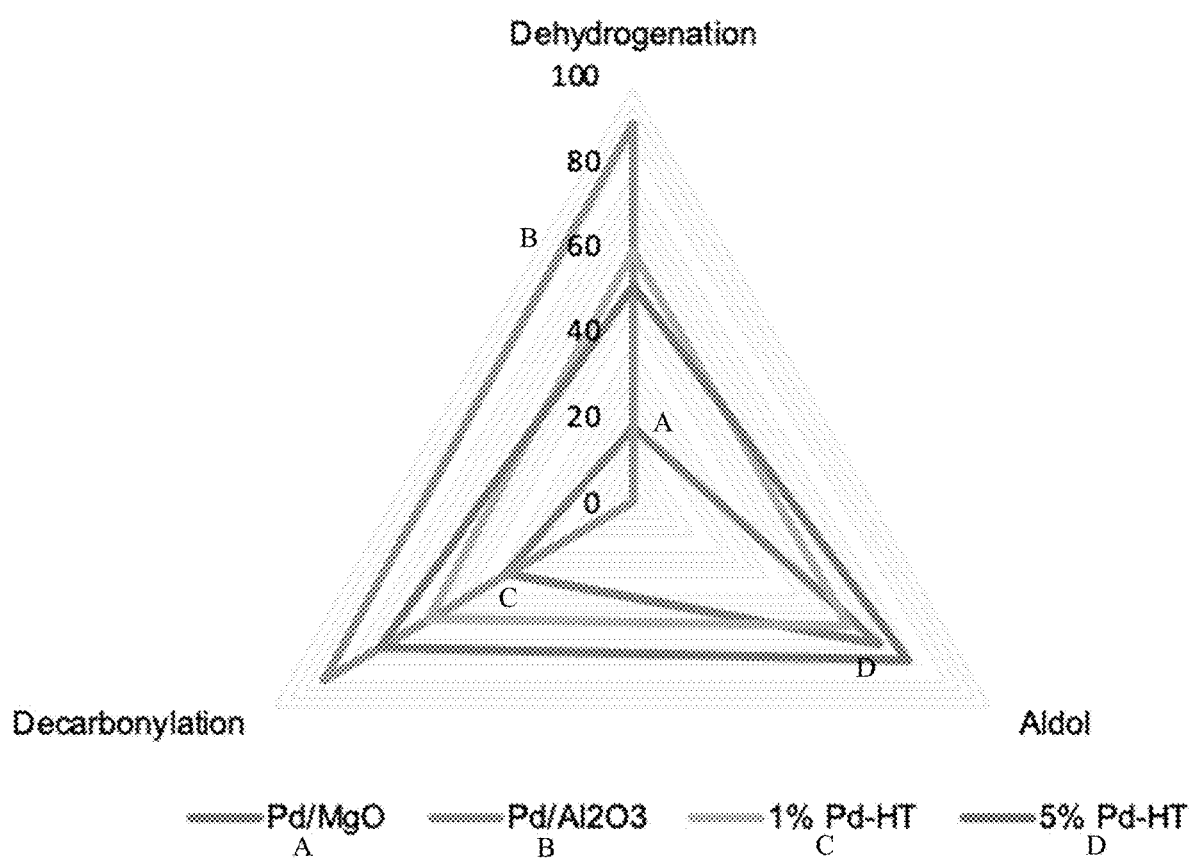
FIG. 9 shows a radial plot of catalytic activity for the three-step deoxygenative olefination of alcohols using Pd—MgO, Pd—$Al_2O_3$, 1% Pd-HT and 5% Pd-HT catalysts.

In order to gain insights into catalyst design for this multi-step process, trends for the activity of the catalysts in the three steps (dehydrogenation, aldol condensation and decarbonylation) were investigated. Dehydrogenation activity was assessed from the total conversion, given that all products are derived from dehydrogenation, including ether 2 in the case of Pd—$Al_2O_3$. The trend for dehydrogenation follows Pd-$Al_2O_3$>5% Pd-HT>Pd—MgO. Activity for aldol condensation was assessed from reactions with heptanal at 100° C., where no decarbonylation occurs. Based on the net yields of aldol condensates at 2 hours, the trend for aldol condensation follows Pd-MgO~5% Pd-HT>>Pd—$Al_2O_3$, indicating that the strong basic sites on MgO and HT are significantly more effective for aldol condensation than the Lewis acidic sites of $Al_2O_3$. Trends in decarbonylation activity were assessed from 2-hour reactions with heptanal at 150° C. based on percent of aldol product decarbonylated. Under these conditions, the decarbonylation trend follows Pd—$Al_2O_3$>Pd-HT>Pd—MgO. Comparing this trend to the lower selectivity observed for hydrocarbons 8 and 9 using Pd-HT vs Pd—MgO (Pd-HT: ~3:2 ratio of Guerbet alcohol 5 to 8 and 9, vs Pd—MgO: no alcohol 5), it can be concluded that it is not that Pd-HT is a less efficient decarbonylation catalyst than Pd—MgO, but rather that it facilitates competing transfer hydrogenation of 7. The relative competence of the catalysts for the three steps (see FIG. 9) suggests that obtaining high activity and selectivity for the hydrocarbons requires a balanced catalytic efficiency for each of the three steps and limiting competing ketal hydrogenolysis and transfer hydrogenation.

Figure 10:
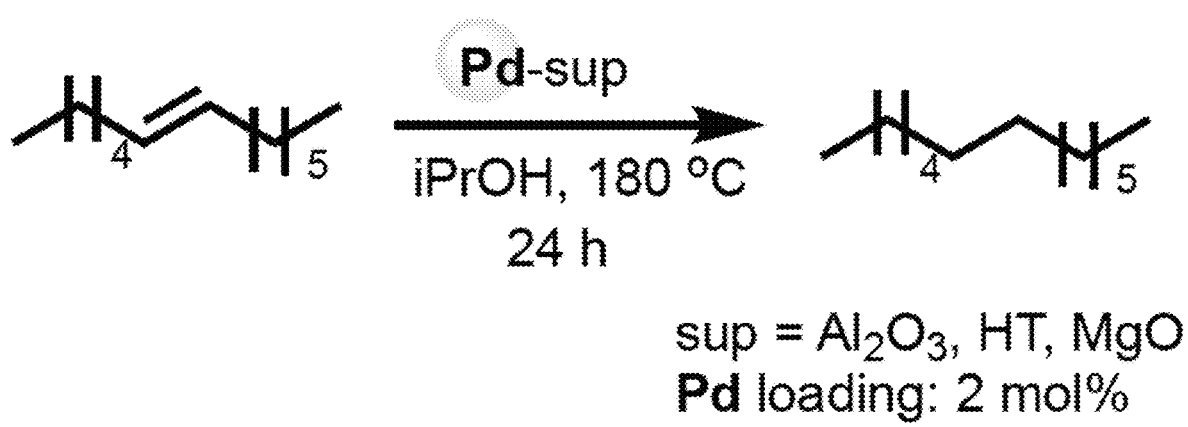
FIG. 10 shows a schematic for the transfer hydrogenation of tridec-6-ene using 2-propanol.

To rationalize the ratio of alkene 8 versus alkane 9, and thus the ability of the catalyst to facilitate transfer hydrogenation of alkenes, the efficiency of the catalysts for the TH of 6-E-tridecene (8 in FIG. 3) using 2-propanol as hydrogen donor was investigated (see FIG. 10). Pd—MgO afforded~4-fold lower yield of alkane than Pd-HT (15% vs 62%), consistent with the lower fraction of 9:8 afforded by Pd—MgO in the heptanol reaction (1:1.7 for and 1:3.4 with Pd—MgO and Pd-HT respectively, see FIG. 8). This trend is also consistent with the faster heptanol conversion observed for Pd-HT compared to Pd—MgO. Pd—$Al_2O_3$ affords 51% yield of 9, suggesting it too is an efficient TH catalyst.

Figure 8:
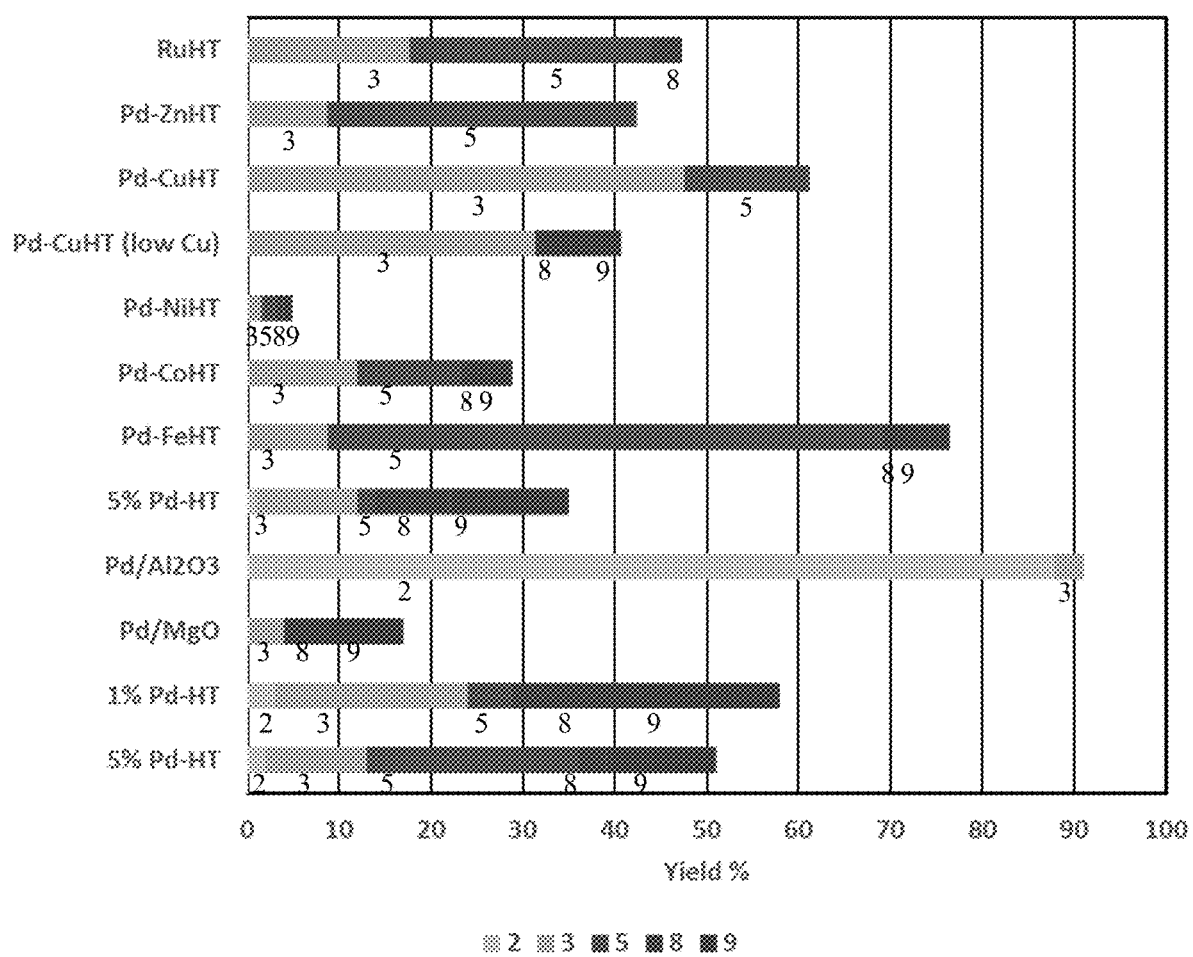
FIG. 8 shows the product yield and selectivity for deoxygenative olefination of n-heptanol coupling over supported palladium catalysts. See FIG. 3 for product structures.

However, as previously discussed, Pd—$Al_2O_3$ favors formation of ether 2, and hence does not form hydrocarbons (see FIG. 8). In a similar experiment with aldol product 7, Pd-HT (1% and 5%) was found to be ~2-fold more active than Pd—MgO for formation of alcohol 5. Thus, the selectivity of Pd—MgO for 8 and 9 over 5 is the result of its faster decarbonylation and slower TH relative to that of Pd-HT.

Elemental analysis of the post-reaction (used) Pd-HT shows a small loss of Pd and Mg (<10%). HRTEM images of this used (post reaction) catalyst do not indicate extensive morphological changes, but do show a small increase in mean particle size, from 2.4 to 3.4 nm nanoparticles, and a broadening of the particle size distribution. HRTEM identified two Pd phases: reduced Pd(111), and PdO(101). Powder XRD of the used Pd-HT does not show reflections of Pd phases. To determine whether decarbonylation was driven by soluble Pd species, poisoning tests were conducted with 1,10-phenanthroline as a scavenger of soluble Pd. Addition of 5 equivalents of 1,10-phenanthroline relative to total Pd resulted in a 22% reduction of activity, suggesting catalysis is predominantly heterogeneous for Pd-HT. A hot filtration test was also performed by sampling a portion of the reaction mixture after 3 hours and passing this through a 2 μm hot frit. Product concentrations of the filtrate did not change significantly over the following 5 hours, evidencing catalytically competent soluble species.

EXAMPLES

Materials and Characterization

Aluminium (III) nitrate nonahydrate (98%) and magnesium (II) nitrate tetrahydrate (98%) were obtained from ACROS Organics. Sodium hydroxide (97%) was obtained from VWR AMRESCO® Life Sciences; sodium carbonate (99.5%) was obtained from Fisher. Palladium (II) nitrate hydrate (40% palladium basis), palladium (II) acetate (98%) and 4-acetylbenzaldehyde (97%) were purchased from Sigma Aldrich. 1-Heptanol (>98%), heptanal (>95%) and 1,3,5-trimethoxybenzene (>98%) were obtained from TCI America. Isopropanol (HPLC grade) was obtained from Fischer Scientific, and tert-butanol (99.5%) was obtained from ACROS Organics.

Elemental analysis was carried out with inductively coupled plasma atomic emission spectroscopy (ICP-AES) on a Shimadzu ICPE-9820 Plasma Atomic Emission Spectrometer. Powder X-Ray Diffraction (PXRD) patterns were obtained using a Rigaku MiniFlex II X-Ray diffractometer, between 2θ of 0-80°. XPS data was collected both using MgKα (1253.6 eV) anode and monochromatic Al (1486.7 eV) X-ray sources at 240 W and 40 eV pass energy. Charge neutralization was carried out to minimize surface charging. Hydrocarbon C is binding energies were referenced at 284.8 eV. Pd 3d binding energies were confirmed by Mg anode due to the overlapping of Magnesium Auger Electron peaks (Mg KLL) with Pd 3d signals when Al anode was used. Binding energies of other elements were confirmed using the monochromatic Al X-ray source. Transmission Electron Microscope (TEM) images were collected on Talos F200X under 200 kV FEG with Ceta 16M camera. Fast Energy-dispersive X-ray spectroscopy (EDS) mapping was carried out using the built-in Silicon Drift Detector (Super-X EDS Detector). Nitrogen isotherms were measured on a Micrometric TriStar surface analyzer at liquid nitrogen temperature. Samples were degassed under vacuum at 150° C. for 3 hours prior to measurement. Surface area was calculated using the BET method.

NMR spectra were recorded on an Agilent 400 MHz spectrometer.

GC-MS analyses were performed on a Shimadzu QP2010S GC-MS fitted with a SHRXI-5MS column with dimensions L=30 m, ID=0.25 and DF=0.25, run in positive ion mode.

Temperature programmed desorption (TPD) measurements were performed using a Micromeritics AutoChem II. For determination of basic sites, the catalysts were first calcined by heating at a rate of 10° C. $min^{-1}$ in flowing He (99.999%) and then held for 1 hour at 700° C. The release of gas from the catalyst during this step was monitored by the TCD detector. Following calcination, the sample was cooled to room temperature (RT) and exposed to flowing $CO_2$ (Airgas, 99.99%) for 2 hours. The system was then purged with He carrier gas for 1 hour, or until a stable baseline was observed, to remove weakly adsorbed $CO_2$. The temperature of the sample was then increased at a rate of 10 K $min^{-1}$ from RT to 700° C. to desorb $CO_2$ from the catalyst surface. For determination of acidic sites, the $CO_2$ in the above method was replaced with a 10% $NH_3$ (99.999%) in He (99.999%) mixture from Praxair with all other steps remaining the same.

Catalyst Synthesis

Pd—$Al_2O_3$ was synthesized via wet impregnation as follows. γ-Alumina (Aldrich, 1 g) was calcined at 450° C. in a muffle furnace for 12 hours, then suspended in deionized (DI) water (10 mL). Palladium nitrate (0.2153 g) was dissolved in 100 mL DI water at room temperature, then added dropwise to the stirred alumina suspension. The slurry was stirred for a further 2 hours, filtered through grade 410 filter paper, and the residue then dried for 12 hours at 110° C. The resulting solid was then calcined at 450° C. under static conditions for 12 hours and stored in a desiccator.

Pd-HT and doped Pd-xHT were synthesized via a continuous flow method. A nitrate salt solution of $Mg(NO_3)_2 \cdot 6H_2O$ (3.590 g), $Al(NO_3)_3 \cdot 9H_2O$ $6H_2O$ (1.876 g), and $Pd(NO_3)_2 \cdot xH_2O$ (0.230 g) was dissolved in 70 mL of deionized (DI) water. A base solution comprising NaOH (0.040 mol) and $Na_2CO_3$ (0.0025 mol) was dissolved in 70 mL of DI water. The two solutions were mixed in a continuous fashion using syringe pumps (KD Scientific model 230) connected with a Y-connector at a flow rate of 4 mL/min. The solution mixture was dropped into a beaker containing 100 mL of DI water with stirring (200 rpm). The mixture was aged at 65° C. for 2 hours, then cooled to room temperature, filtered, and washed with DI water until the pH of the filtrate was neutral. The resulting powder was dried in air at 110° C. for 12 hours and stored in a desiccator.

Pd—MgO was synthesized via wet impregnation using a modified protocol reported by Akuri et al., *Catal. Lett.*, 147, 1285-129, 2017. 600 mL of a 1M solution of $Mg(NO_3)_2 \cdot 6H_2O$ was mixed with 800 mL of a 0.0312 M solution of NaOH in a continuous fashion using syringe pumps connected with a Y-connector at a flow rate of 4 mL/min. The solutions were deposited into a beaker containing 100 mL of DI water while stirring at 200 rpm. The pH of the solution was adjusted to 10±0.1 by addition of NaOH solution, and the mixture was aged at 60° C. for 1 hour. The suspension was further stirred at room temperature for 12 hours. The slurry was then filtered, and the resulting solid dried in a laboratory oven for 12 hours at 110° C. The solid was then calcined at 450° C. for 12 hours in a furnace. The calcined solid was suspended in DI water (10 mL). Palladium nitrate (0.1082 g, Aldrich) was dissolved in 10 mL DI water at room temperature, then added dropwise to the stirred suspension. After completing the addition, the solution was stirred for 2 hours. The slurry was then filtered, and the impregnated solid dried at 110° C. for 12 hours, calcined at 450° C. for 12 hours under static conditions, then stored in a desiccator.

Figure 11:
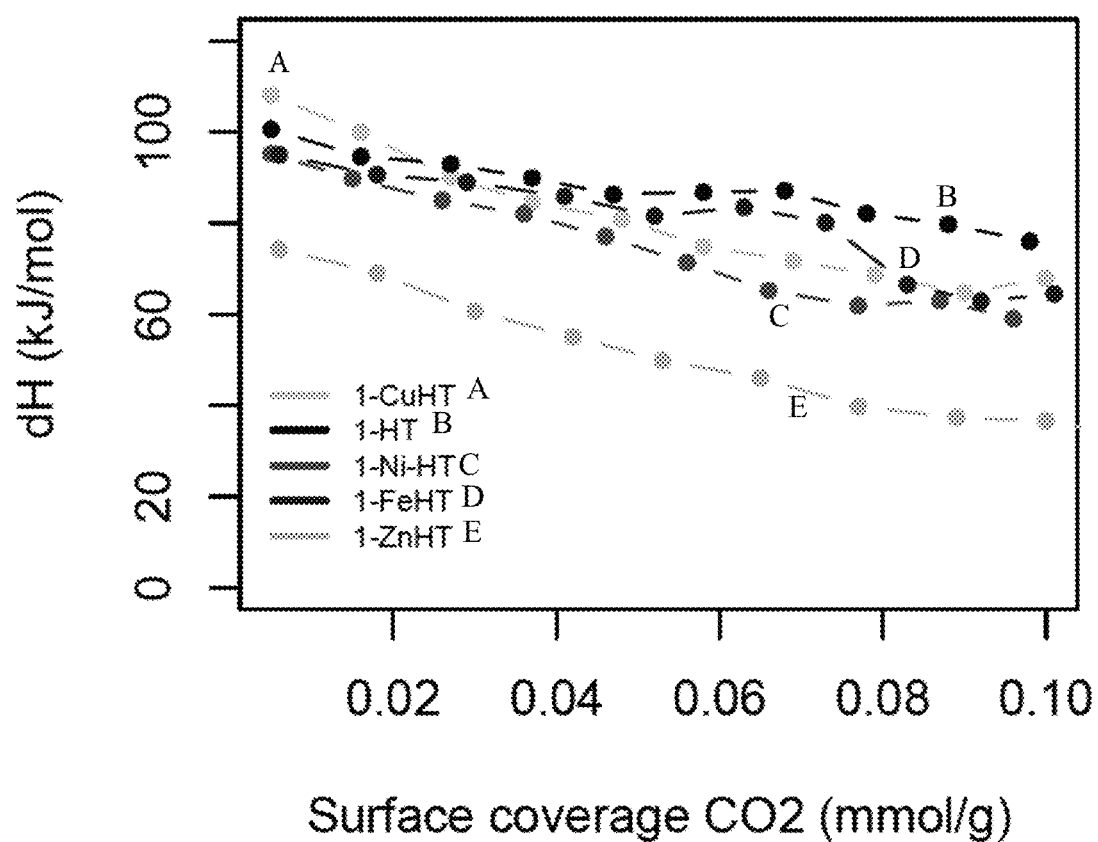
FIG. 11 shows the differential enthalpy of adsorption as a function of coverage for the adsorption of $CO_2$ on Pd-HT (5%) and Cu, Ni, Fe and Zn doped Pd-HT (5%) hydrotalcite supports.

FIG. 11 shows the differential enthalpy of adsorption as a function of coverage for the adsorption of $CO_2$ on Cu, Ni. Fe and Zn doped hydrotalcite supports.

Table 3 shows the characterization of Pd-HTs and control HT (elemental composition and PXRD crystallographic parameters (a, c and L).

TABLE 3

| Catalyst | Elemental composition, metal mol %[a] | | | | Crystallographic parameters | | |
|---|---|---|---|---|---|---|---|
| | $Pd^{2+}$ | $Mg^{2+}$ | $Al^{3+}$ | $M^{2+}/M^{3+}$ | a (Å)* | c (Å)* | L (nm) |
| 5% Pd—HT | 5.15 | 70.1 | 25.1 | 2.98 | 3.052 | 23.07 | 10.4 |
| 1% Pd—HT | 0.99 | 73.8 | 25.2 | 2.97 | 3.003 | 23.56 | 10.6 |
| Mg—Al (HT) | — | 75.6 | 24.4 | 3.09 | 3.066 | 23.35 | 10.8 |

[a]Mol % calculated as fraction of all metals present (Mg, Al, Pd); *a, the average cation-cation distance; *c, three times the distance from the center of one brucite-like layer to the next layer; L, the average crystallite size (calculated using Scherrer's formula).

Figure 12A:
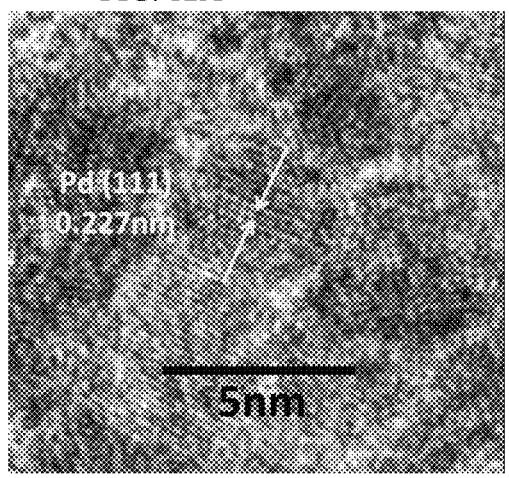
FIG. 12 shows the HRTEM (High resolution TEM) and crystal lattice of 5% Pd-HT (FIG. 12a) showing Pd (111), 5% Pd-HT (FIG. 12b) showing PdO (110) phase, and 1% Pd-HT (FIG. 12c) showing Pd (111) phase.
Figure 12B:
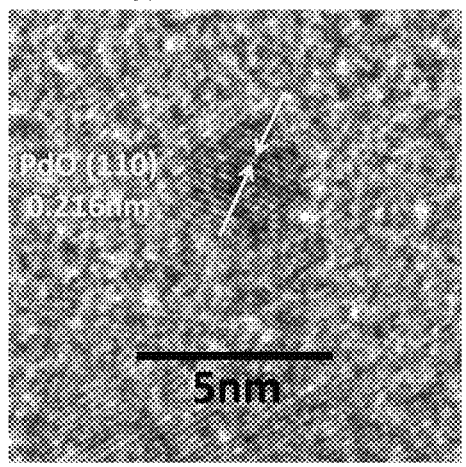
Figure 12C:
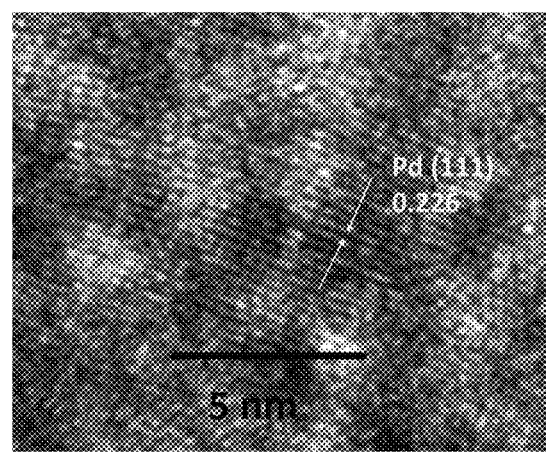

FIG. 12 shows the HRTEM and crystal lattice of (a) 5% Pd-HT showing Pd (111); (b) 5% Pd-HT showing PdO (110) phase and (c) 1% Pd-HT showing Pd (111) phase.

Figure 13A:
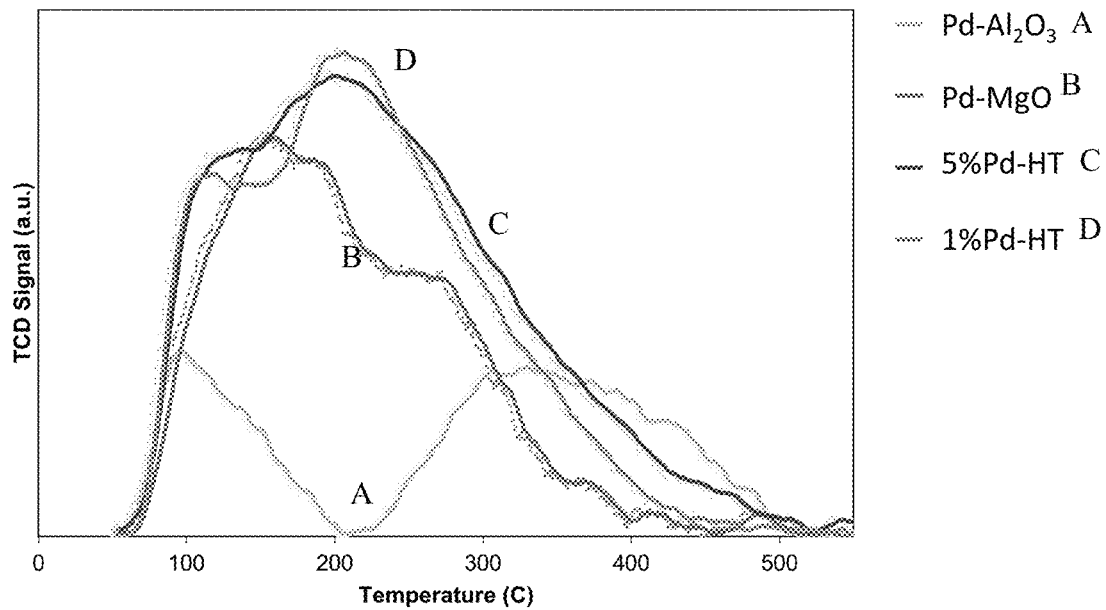
FIG. 13 shows temperature-programmed desorption profiles of Pd—MgO, Pd—$Al_2O_3$, 1% Pd-HT and 5% Pd-HT catalysts using $CO_2$ (FIG. 13a) and $NH_3$ (FIG. 13b) as probes for solid base and acid sites, respectively.
Figure 13B:
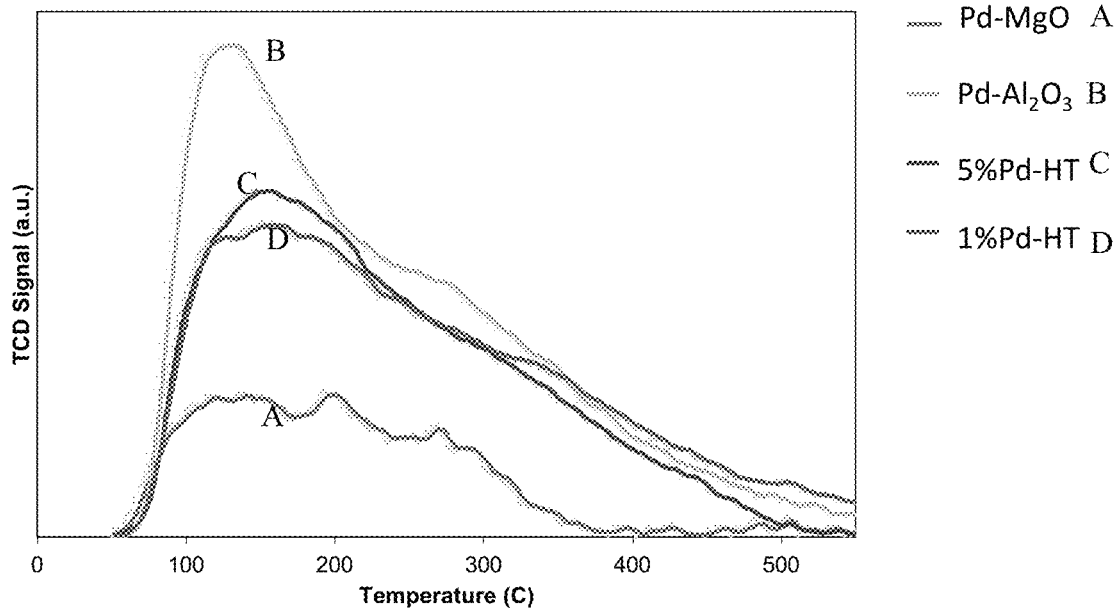

FIG. 13 shows the temperature-programmed desorption profiles of four supported Pd catalysts (Pd—O, Pd—$Al_2O_3$, %% Pd-HT and 1% Pd-HT) using (a) $CO_2$ and (b) $NH_3$ as probes for solid base and acid sites, respectively.

Deoxygenative Heptanol Olefination

A 20-mL reaction tube was charged with a magnetic stir bar, catalyst (mass adjusted to provide 0.028 mmol Pd loading) and heptanol (Millipore Sigma, >98% 2 mL, 14.17 mmol). The mixture was sealed in a 20-mL reaction tube and heated to 180° C. and stirred under air for the time indicated on a Heidolph Radleys Carousel 12 Plus Reaction Station. The tridecane amount was quantified using GC-FID with 1,3,5-trimethoxybenzene as the internal standard. The yields for all other products were determined by $^1$H NMR using 1,3,5-trimethoxybenzene as the internal standard. Qualitative product characterization was also characterized by GC-MS.

Table 4 shows the product yields and conversion for n-heptanol deoxygenative olefination over supported Pd catalysts. See FIG. 3 for product structures.

TABLE 4

| | 2 | | 3 | | 5 | | 8 | | 9 | | |
|---|---|---|---|---|---|---|---|---|---|---|---|
| Catalyst | y. % | sel. % | y. % | sel. % | y. % | sel. % | y. % | sel. % | y. % | sel. % | Conv. % |
| Pd—HT | 3 | 5 | 21 | 61 | 5 | 9 | 14 | 25 | 15 | 27 | 58 ± 3 |
| Pd—MgO | 0 | 0 | 4 | 30 | 0 | 0 | 5 | 47 | 8 | 29 | 17 ± 2 |
| Pd—$Al_2O_3$ | 88 | 97 | 3 | 3 | 0 | 0 | 0 | 0 | 0 | 0 | 91 ± 3 |
| 5% Pd—HT | 2 | 4 | 11 | 29 | 23 | 47 | 3 | 6 | 12 | 25 | 51 ± 3 | y.: Yield, sel.: Selectivity; Conditions: 2 mL n-heptanol, 0.2 mol % Pd-support, 180° C., 48 h. Yields and conversion based on GC-FID and NMR quantitation with 1,3,5-trimethoxybenzene as the internal standard. Standard errors are based on two runs.

Scheme 1

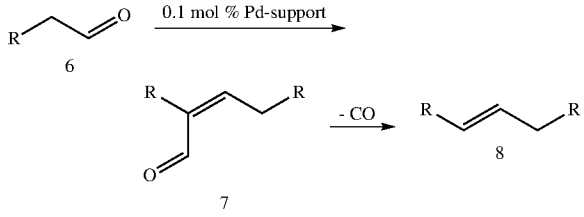

$R = C_5H_{11}$

FIG. 14 shows the time course of decarbonylative olefination of heptanal (see Scheme 1) using (a) 5% Pd-HT, (b) Pd—$Al_2O_3$ and (c) Pd—MgO at 100° C.

FIG. 15 shows the time course of decarbonylative olefination of heptanal using (a) Pd-HT, (b) Pd—$Al_2O_3$ and (c) Pd—MgO at 150° C., under air. Trends in decarbonylation activity were assessed from each time point based on percent of total aldol product decarbonylated, calculated as follows:

$$\text{Total aldol product decarbonylated} = \frac{\text{Yield}(8)}{\sum \text{Yields}(7, 8)} \times 100\%$$

The effective decarbonylation yields are shown in Table 5 be:

TABLE 5

| | Effective Decarbonylation Yield % | | |
|---|---|---|---|
| Reaction time (hr) → | 2 | 8 | 24 |
| Pd-HT | 15 | 15 | 68 |
| Pd-MgO | 13 | 10 | 34 |
| Pd-$Al_2O_3$ | 20 | 40 | 83 |

Table 6 shows the relative catalytic activity for the three-step reactions involved in deoxygenative coupling of heptanol. Dehydrogenation is calculated from conversion to products 2, 3, 5, 8 and 9 using conditions described in FIG. 3. Aldol condensation is calculated from the 2-hour yield of 7 at 100° C. (see FIG. 13). Decarbonylation yield is calculated from ratio of 8 to the sum of 7 and 8, as described above.

TABLE 6

| Catalyst | Dehydrogenation | Aldol condensation | Decarbonylation |
|---|---|---|---|
| Pd-HT | 58% | 58% | 62% |
| Pd/MgO | 17% | 66% | 34% |
| Pd/Al$_2$O$_3$ | 88% | 0% | 83% |
| 5% Pd-HT | 50% | 74% | 68% |

Table 7 shows the elemental composition of Pd-HT (5%) and used Pd-HT (ICP-AES)

TABLE 7

| Catalyst | Pd wt. % | Mol (±RSD) % | | |
|---|---|---|---|---|
| | | Pd | Mg | Al |
| Pd-HT | 5.15 | 4.62 ± 0.29 | 69.82 ± 0.31 | 25.56 ± 0.32 |
| Used Pd-HT | 4.65 | 6.80 ± 0.56 | 66.23 ± 0.15 | 26.97 ± 0.35 |

FIG. 16 shows (a) the TEM image of used Pd-HT (5%) and (b) the corresponding particle size distribution of used Pd-HT. The mean particle size: 3.3±0.5 nm. $^1$H NMR data for products depicted in 4G. 3 are provided below, Product 2: di(n-heptyl) ether
$^1$H NMR (400 MHz, CDCl$_3$) δ 3.39 (m, 4H), 1.22-1.64 (broad, 20H), 0.88 (t, 6H).
ESI-MS: 214 m/z.

Product 3: n-heptyl heptanoate.
$^1$H NMR (400 MHz, CDCl$_3$) δ 4.01 (t, 2H), 2.25 (t, 2H), 1.57 (m, 4H), 1.32 (m, 14H), 0.85 (t, 6H).

Product 5: 2-pentyl-1-nonanol
$^1$H NMR (400 MHz, CDCl$_3$) δ 3.70-3.53 (m, 2H), 1.46-1.28 (broad, 22H), 0.90-0.86 (m, 6H).

Product 6: heptanal
$^1$H NMR (400 MHz, CDCl$_3$) δ 9.33 (s, 1H), 1.81 (t, 2H), 1.31-1.03 (m, 8H), 0.82 (t, 3H).

Product 7: 2-pentyl-2-nonenal.
$^1$H NMR (400 MHz, CDCl$_3$) δ 9.33 (s, 1H), 6.40 (t, 1H), 2.34 (m, 2H), 2.26-2.17 (m, 2H), 1.53-1.45 (m, 2H), 1.40-1.25 (m, 12H), 0.92-0.83 (t, 6H).

Product 8: (6E)-Tridecene
$^1$H NMR (400 MHz, CDCl$_3$) δ 5.40-5.33 (m, 2H), 2.03-1.97 (m, 4H), 1.30-1.20 (m, 14H), 0.94-0.86 (t, 6H).

Product 9: Tridecane.
$^1$H NMR (400 MHz, CDCl$_3$) δ 1.38-1.25 (m, 22H), 0.94-0.86 (t, 6H).

The description of the present embodiments of the invention has been presented for purposes of illustration but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention.

All patents and publications cited herein are incorporated by reference in their entirety.

What is claimed is:

1. A process for preparing a hydrocarbon comprising:
   reacting an alcohol, and aldehyde, or both, with a catalyst to form a hydrocarbon;
   wherein the catalyst comprises palladium and a support, wherein the support is selected from magnesium oxide, hydrotalcite, montmorillonite, vermiculite, kaolinite, talc, nontronite, saponite, illite, amosite, chamosite, cookeite, nimite, dickite, nacrite, pyrophyllite, and any combination thereof, and
   wherein the particle size of the support ranges between about 10 nm and about 400 nm.

2. The process of claim 1, wherein the process is conducted in the absence of a solvent.

3. The process of claim 1, wherein the process is conducted in the presence of a solvent.

4. The process of claim 1, wherein the alcohol is a primary alcohol, a secondary alcohol, a tertiary alcohol, a diol, a polyol, or any combination thereof.

5. The process of claim 1, wherein, the alcohol is an aliphatic alcohol having a methylene (—CH$_2$—) group adjacent to the hydroxyl bearing carbon atom.

6. The process of claim 1, wherein the alcohol in selected from methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, heneicosanol, docosanol, tricosanol, tetracosanol, pentacosanol, hexacosanol, heptacosanol, octacosanol, nonacosanol, triacontanol, glycerol, hexitol, sorbitol, 1,2-butadiol, 1,4-butadiol, arabinol, xylose, 2-deoxyhexopyranose, 1,4-anhydroxylitol, 1,5-gluconolactone, and any combination of any of the foregoing.

7. The process of claim 1, wherein the particle size of the palladium ranges between about sub-nano and about 10 nm.

8. The process of claim 1, wherein the support is a basic support, an acidic support, an amphoteric support, or any combination thereof.

9. The process of claim 1, wherein the support comprises magnesium oxide, hydrotalcite, or a combination thereof.

10. The process of claim 1, wherein the catalyst comprises between about 0.1 mol. % and about 10 mol % of palladium.

11. The process of claim 1, wherein the support further comprises a dopant.

12. The process of claim 11, wherein the dopant comprises a metal selected from Fe, Cu, Ni, Zn, Co, or any combination thereof.

13. The process of claim 1, wherein the process comprises a deoxygenative coupling reaction.

14. The process of claim 1, wherein the process comprises a tandem dehydrogenation, aldol condensation and decarbonylation reaction.

15. A hydrocarbon prepared by a process according to claim 1.

16. A fuel prepared by a process according to claim 1.

17. A process for preparing a hydrocarbon comprising:
reacting an alcohol, and aldehyde, or both, with a catalyst to form a hydrocarbon;
wherein the catalyst comprises palladium and a support, and
wherein the process is conducted in a solvent selected from toluene, tetrahydrofuran, ethanol, and any combination thereof.

18. The process of claim 17, wherein the particle size of the support ranges between about 10 nm and about 400 nm.

19. A process for preparing a hydrocarbon comprising:
reacting an alcohol, and aldehyde, or both, with a catalyst to form a hydrocarbon;
wherein the catalyst comprises palladium and a support,
wherein the support is selected from magnesium oxide, hydrotalcite, montmorillonite, vermiculite, kaolinite, talc, nontronite, saponite, illite, amosite, chamosite, cookeite, nimite, dickite, nacrite, pyrophyllite, and any combination thereof,
wherein the process is conducted in the presence of a solvent, and
wherein the solvent is selected from toluene, tetrahydrofuran, ethanol, and any combination thereof.

* * * * *